(12) United States Patent
Benabdillah et al.

(10) Patent No.: US 9,610,230 B2
(45) Date of Patent: *Apr. 4, 2017

(54) AQUEOUS COSMETIC COMPOSITION COMPRISING ONE OR MORE VINYLFORMAMIDE/VINYLAMINE COPOLYMERS, ONE OR MORE NON-SILICONE FATTY SUBSTANCES, ONE OR MORE SURFACTANTS AND ONE OR MORE SILICONES

(75) Inventors: Katarina Benabdillah, St-Jean du Pin (FR); Estelle Mathonneau, Paris (FR)

(73) Assignee: L'OREAL, Paris (FR)

( * ) Notice: Subject to any disclaimer, the term of this patent is extended or adjusted under 35 U.S.C. 154(b) by 391 days.

This patent is subject to a terminal disclaimer.

(21) Appl. No.: 12/362,837

(22) Filed: Jan. 30, 2009

(65) Prior Publication Data

US 2009/0269295 A1   Oct. 29, 2009

Related U.S. Application Data

(60) Provisional application No. 61/064,418, filed on Mar. 5, 2008.

(30) Foreign Application Priority Data

Jan. 31, 2008  (FR) ..................... 08 50631

(51) Int. Cl.
*A61K 8/81* (2006.01)
*A61Q 5/06* (2006.01)
*A61K 8/31* (2006.01)
*A61K 8/06* (2006.01)
*A61Q 5/12* (2006.01)

(52) U.S. Cl.
CPC ................. *A61K 8/31* (2013.01); *A61K 8/06* (2013.01); *A61K 8/817* (2013.01); *A61Q 5/06* (2013.01); *A61Q 5/12* (2013.01)

(58) Field of Classification Search
CPC . A61K 8/31; A61K 8/06; A61K 8/817; A61Q 5/06; A61Q 5/12
USPC ......... 424/70.9, 70.17; 8/442, 405; 132/202, 132/208
See application file for complete search history.

(56) References Cited

U.S. PATENT DOCUMENTS

| | | | |
|---|---|---|---|
| 2,528,378 A | 10/1950 | Mannheimer et al. | |
| 2,781,354 A | 2/1957 | Mannheimer et al. | |
| 4,342,744 A | 8/1982 | Arai et al. | |
| 4,713,236 A | 12/1987 | Hoover et al. | |
| 4,764,363 A | 8/1988 | Bolich, Jr. | |
| 5,324,506 A | 6/1994 | Calvo et al. | |
| 5,632,977 A | 5/1997 | Chandran et al. | |
| 5,753,759 A | 5/1998 | Hartmann et al. | |
| 6,630,133 B1 | 10/2003 | Dupuis | |
| 2003/0199652 A1 | 10/2003 | Schneider et al. | |
| 2005/0053569 A1* | 3/2005 | Bavouzet ................. A61K 8/06 424/70.17 |
| 2005/0129646 A1 | 6/2005 | Vic et al. | |
| 2005/0245684 A1 | 11/2005 | Daniel et al. | |
| 2005/0276777 A1 | 12/2005 | Lalleman et al. | |
| 2006/0100114 A1* | 5/2006 | Molenda ................. A61K 8/362 510/119 |
| 2006/0286057 A1 | 12/2006 | Cannell et al. | |
| 2007/0107141 A1* | 5/2007 | Nguyen et al. ................. 8/405 |
| 2007/0110690 A1* | 5/2007 | Nguyen et al. ............. 424/70.1 |
| 2008/0182773 A1* | 7/2008 | Gauweiler ............... A61K 8/72 510/475 |
| 2008/0299154 A1* | 12/2008 | Barrios et al. ................. 424/401 |
| 2009/0202465 A1 | 8/2009 | Mougin et al. | |

FOREIGN PATENT DOCUMENTS

| | | |
|---|---|---|
| DE | 19540853 A1 | 5/1997 |
| DE | 10 2005 014 293 A1 | 9/2006 |
| EP | 1 779 894 A1 | 5/2007 |
| JP | 2002-255756 | 9/2002 |
| WO | WO 96/03969 A1 | 2/1996 |
| WO | WO 02/15854 A1 | 2/2002 |
| WO | WO 2006/048169 A1 | 5/2006 |
| WO | WO 2006/100299 A1 * | 9/2006 |
| WO | WO 2007/003784 A1 | 1/2007 |

OTHER PUBLICATIONS

Liquid Petrolatum: [online], [retrieved on Apr. 1, 2011], retrieved from http://www.merriam-webster.com/medical/liquid %20petrolatum.*
Polyquaternium 10: retrieved from internet: http://www.saapedia.org/en/saa/?type=detail&id=3743. Retrieved on Sep. 23, 2015.*
Polyquaternium-11: retrieved frominternet: http://www.tu-poly.com/p832/Polyquaternium-11,CAS-No. 53633-54-8.html. Retrieved on Apr. 29, 2016.*
French Search Report for FR 0850631, dated Sep. 23, 2008.
English language abstract of EP 1 779 894 A1, May 2, 2007.
English language abstract of JP 2002-255756, Nov. 9, 2002.
English language Abstract of DE 19540853 A1 dated May 7, 1997.
French Search Report for FR 07/54210, dated Nov. 13, 2007.
French Search Report for FR 08/50607, dated Sep. 24, 2008.
Copending U.S. Appl. No. 12/362,848, filed Jan. 30, 2009.
Office Action mailed Oct. 5, 2011, in co-pending U.S. Appl. No. 12/362,848.
Copending U.S. Appl. No. 12/078,584, filed Apr. 2, 2008.
Office Action mailed Jan. 21, 2011, in co-pending U.S. Appl. No. 12/078,584.
Office Action mailed Jul. 7, 2011, in co-pending U.S. Appl. No. 12/078,584.

\* cited by examiner

*Primary Examiner* — Hong Yu
(74) *Attorney, Agent, or Firm* — The Marbury Law Group, PLLC

(57) ABSTRACT

A cosmetic composition containing in a cosmetically acceptable aqueous medium:
one or more non-silicone fatty substances,
one or more surfactants,
one or more vinylformamide/vinylamine copolymers, and
one or more silicones.
Can be used for the styling of the hair and can make possible to obtain a lasting hold of the hairstyle and also hair conditioning properties.

23 Claims, No Drawings

AQUEOUS COSMETIC COMPOSITION COMPRISING ONE OR MORE VINYLFORMAMIDE/VINYLAMINE COPOLYMERS, ONE OR MORE NON-SILICONE FATTY SUBSTANCES, ONE OR MORE SURFACTANTS AND ONE OR MORE SILICONES

This application claims benefit of U.S. Provisional Application No. 61/064,418, filed Mar. 5, 2008, the contents of which are incorporated herein by reference. This application also claims benefit of priority under 35 U.S.C. §119 to French Patent Application No. FR 0850631, filed Jan. 31, 2008, the contents of which are also incorporated herein by reference.

The present disclosure relates to an aqueous cosmetic composition comprising, in a cosmetically acceptable medium, one or more non-silicone fatty substances, one or more surfactants, one or more vinylformamide/vinylamine copolymers and optionally one or more silicones.

The present disclosure also relates to the use of this composition in hair cosmetic treatment, in particular for hair styling and hair care, and to a method for the cosmetic treatment of the hair employing such a composition.

Finally, the present disclosure relates to a method for fixing and/or shaping the hair which employs an aqueous cosmetic composition comprising, in a cosmetically acceptable medium, one or more non-silicone fatty substances, one or more surfactants and one or more vinylformamide/vinylamine copolymers.

Styling products are normally used to build or structure the hairstyle and to provide it with lasting hold. They are usually provided in the form of lotions, gels, foams, creams, sprays, and the like. The corresponding compositions generally comprise one or more film-forming polymers or "fixing polymers" in a cosmetically acceptable medium. These polymers make possible the formation of a sheathing film on the individual hairs, thus ensuring the form retention of the hairstyle.

However, the fixing polymer films thus formed may have the disadvantage of being relatively friable, which limits the hold of the hairstyle over time and results in the formation, on the hair, of unsightly residues.

Thus, conventional styling products may result in a fixing of the hairstyle and styling effects which gradually fade over time. In particular, when the product is applied in the morning, the styling effects fade as the day progresses. On the following morning, the styling effects are slight, indeed even nonexistent.

This problem may be greater when it is a matter of styling and shaping curly hair or "ethnic" hair, that is to say hair of, for example, Brazilian, African or Maghrebian type, which can exhibit the distinctive feature of being generally dry and curly, and particularly difficult to shape.

It is known, in order to solve this problem, to incorporate polymers with a very high fixing power in the styling products and/or to increase the concentration of fixing polymer. However, the use of such highly fixing products may lead to a number of disadvantages. In particular, these products generally do not make it possible to have sufficient cohesion of the locks with one another, result in a dry and rough feel of the hair and are difficult to remove on shampooing.

A need thus exists for hair compositions which make it possible to obtain a strong fixing, with a sufficient cohesion of the locks (without separation into isolated strands), and a lasting fixing of the hairstyle, with styling effects which last throughout the day, indeed even several days, while being easily removed on shampooing and while providing a pleasant cosmetic feel.

International Patent Application WO 96/03969 describes in a general way cosmetic compositions intended for the fixing and/or conditioning of the hair which comprise a vinylformamide homopolymer or a copolymer of vinylformamide and of one or more other vinyl monomers, in combination with at least one ingredient chosen from conditioning agents, emulsifying agents, surfactants, viscosity modifiers, gelling agents, opacifying agents, stabilizing agents, preservatives, sequestering agents, chelating agents, pearlescent agents, clarifying agents, fragrances, colorants, propellants, organic solvents and water.

Furthermore, U.S. Pat. No. 4,421,602 describes vinylformamide/vinylamine copolymers, their preparation and their use in the paper industry for improving the retention, the rate of flow and the flocking.

It has now been discovered that, surprisingly, the combination in an aqueous medium of a vinylformamide/vinylamine copolymer with a non-silicone fatty substance and a surfactant makes it possible to obtain a hair cosmetic composition which has improved styling properties.

For example, such a combination makes it possible to obtain styling products which provide a fixing of the hairstyle which is strong, with sufficient cohesion of the locks (no separation into isolated strands), and lasting while being easily removed on washing and while providing a pleasant cosmetic feel of the hair.

The present disclosure thus makes it possible to prepare styling products which provide very high degrees of fixing, a very long hold of the hairstyle over time and good resistance of the latter to mechanical stresses.

The present disclosure also makes it possible to prepare styling products which provide a particularly soft and pleasant feel of the hair and particularly fine hair.

The properties of such a composition can be improved when the latter additionally comprises one or more silicones.

An embodiment of the present invention is thus a cosmetic composition comprising, in a cosmetically acceptable aqueous medium:

one or more non-silicone fatty substances,
one or more surfactants,
one or more vinylformamide/vinylamine copolymers comprising:
from 20 to 40 mol % of units of following formula A:

and from 60 to 80 mol % of units of following formula B:

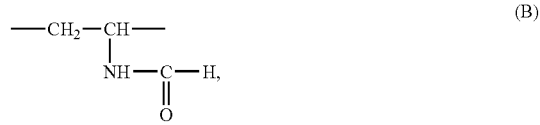

and
one or more silicones.

The compositions according to the disclosure can be particularly appropriate for the styling of curly hair and in particular of ethnic hair, for example of Brazilian, African and Maghrebian type, which exhibits the characteristic of being particularly difficult to shape in a lasting fashion. Thus, the composition according to the disclosure makes it possible, for example, to reduce the volume of the hair or to produce long-lasting flattened hairstyles.

Other possible embodiments, characteristics, aspects and advantages of the invention will become even more clearly apparent on reading the description and examples which follow.

According to one embodiment, the composition comprises, in a cosmetically acceptable aqueous medium, one or more non-silicone fatty substances, one or more surfactants, one or more vinylformamide/vinylamine copolymers and one or more silicones.

The term "cosmetically acceptable medium" is understood to mean a medium compatible with keratinous substances and in particular the hair.

The term "aqueous medium" is understood to mean that the cosmetically acceptable medium used in the compositions according to the present invention is a medium which comprises water.

The composition may comprise, for example, at least 10% by weight of water, with respect to the total weight of the composition. As a further example, the composition comprises at least 20% by weight of water, as even further example, at least 30% by weight and as an even further example, at least 40% by weight, with respect to the total weight of the composition.

The cosmetically acceptable medium can also comprise one or more cosmetically acceptable organic solvents which can in particular be chosen from lower $C_1$-$C_4$ alcohols, such as ethanol, isopropanol, tert-butanol or n-butanol; polyols, such as propylene glycol and glycerol; polyol ethers; $C_5$-$C_{10}$ alkanes; $C_3$-$C_4$ ketones, such as acetone and methyl ethyl ketone; $C_1$-$C_4$ alkyl acetates, such as methyl acetate, ethyl acetate and butyl acetate; dimethoxyethane or diethoxyethane; and their mixtures.

Mention may be made, among the exemplary solvents, of glycerol and ethanol.

The vinylformamide/vinylamine copolymer or copolymers used in certain embodiments comprise from 20 to 40 mol % of units of formula A. In certain embodiments, they can also comprise from 60 to 80 mol % of units of formula B.

The copolymers can be obtained, for example, by partial hydrolysis of polyvinylformamide. This hydrolysis can be carried out in an acidic or basic medium.

The vinylformamide/vinylamine copolymer or copolymers can optionally comprise one or more additional monomer units. In this case, the latter, for example, represent less than 20 mol % of the copolymer.

According to an embodiment, the vinylformamide/vinylamine copolymer or copolymers are composed solely of units of formula A and of units of formula B.

The weight-average molecular weight of the copolymer, measured by light diffraction, can vary from 10000 to 30000000 g/mol, such as from 40000 to 1000000 g/mol and further such as from 100000 to 500000 g/mol.

The cationic charge density of the vinylformamide/vinylamine copolymer can vary from 2 meq/g to 20 meq/g, such as from 2.5 to 15 meq/g and further such as from 3.5 to 10 meq/g.

Mention may be made, as example of vinylformamide/vinylamine copolymers which can be used in the disclosed compositions, inter alia, of the product sold under the Lupamin name by BASF, such as, for example, and without implied limitation, the products provided under the names Lupamin 9030 and Lupamin 9010.

For example, the vinylformamide/vinylamine copolymer or copolymers can be present in the compositions in amounts ranging from 0.05 to 25% by weight, such as from 0.1 to 20% by weight and further such as from 0.5 to 10% by weight, with respect to the total weight of the composition.

The term "fatty substance" is understood to mean, an organic compound which, at ambient temperature (25° C.) and at atmospheric pressure, is insoluble in water (that is to say, exhibits a solubility in water of less than 1% by weight, such as less than 0.5% by weight) and is soluble, under the same conditions of temperature and of pressure, in at least one organic solvent (for example ethanol, chloroform or benzene) to at least 1% by weight.

The non-silicone fatty substances which can be used in the compositions are, for example, all the organic or inorganic and natural or synthetic non-silicone oils, waxes or resins corresponding to this definition.

An oil is a lipophilic compound which is liquid at ambient temperature and which exhibits a reversible solid/liquid change in state.

Mention may be made, as oils which can be used in the composition of the invention, for example, of:

hydrocarbon oils of animal origin, such as perhydrosqualene;

hydrocarbon oils of vegetable origin, such as liquid triglycerides of fatty acids comprising from 4 to 10 carbon atoms, such as triglycerides of heptanoic or octanoic acids, or also, for example, sunflower, maize, soybean, cucumber, grape seed, sesame, hazelnut, apricot, macadamia, arara, castor or avocado oils, triglycerides of caprylic/capric acids, such as, for example, those sold by Stárineries Dubois or those sold under the names Miglyol 810, 812 and 818 by Dynamit Nobel, jojoba oil or shea butter oil;

synthetic esters and ethers, in particular of fatty acids, such as oils of formulae $R^6COOR^7$ and $R^6OR^7$ in which $R^6$ represents a saturated or unsaturated hydrocarbon chain (for example the residue of a fatty acid) comprising from 8 to 29 carbon atoms and $R^7$ represents a branched or unbranched hydrocarbon chain comprising from 3 to 30 carbon atoms; mention may be made, for example, of Purcellin oil, isononyl isononanoate, isopropyl myristate, 2-ethylhexyl palmitate, 2-octyldodecyl stearate, 2-octyldodecyl erucate or isostearyl isostearate; hydroxylated esters, such as isostearyl lactate, octyl hydroxystearate, octyldodecyl hydroxystearate, diisostearyl malate, triisocetyl citrate or heptanoates, octanoates or decanoates of fatty alcohol; polyol esters, such as propylene glycol dioctanoate, neopentyl glycol diheptanoate and diethylene glycol diisononanoate; and pentaerythritol esters, such as pentaerythrityl tetraisostearate;

linear or branched hydrocarbons of mineral or synthetic origin, such as liquid paraffins, which may or may not be volatile, and their derivatives, petrolatum, liquid petrolatum, polydecenes or hydrogenated polyisobutene, such as parleam oil;

fluid fatty alcohols having from 8 to 26 carbon atoms, such as, for example, octyldodecanol, 2-butyloctanol, oleyl alcohol, linoleyl alcohol or linolenyl alcohol;

fluorinated oils which partially comprise hydrocarbon, such as those described in the document JP-A-2 295912. Mention may also be made, as fluorinated oils, of perfluoromethylcyclopentane and perfluoro-1,3-dimethylcyclohexane, for example sold under the names of "Flutec PC1®" and "Flutec PC3®" Y by BNFL Fluorochemicals; perfluoro-1,2-dimethylcyclobutane; perfluoroalkanes, such as dodecafluoropentane and tetradecafluorohexane, for example sold under the names of "PF 5050®" and "PF 5060®" by 3M, or bromoperfluorooctyl, for example sold under the name "Foralkyl®" by Atochem; nonafluoromethoxybutane, for example sold under the name "MSX 4518®" by 3M, and nonafluoroethoxyisobutane; or perfluoromorpholine derivatives, such as 4-(trifluoromethyl)perfluoromorpholine, for example sold under the name "PF 5052®" by 3M.

The term "hydrocarbon oil" in the list of the oils mentioned above is understood to mean any oil comprising predominantly carbon and hydrogen atoms and optionally ester, ether, fluorinated, carboxylic acid and/or alcohol groups.

A wax is a lipophilic compound which is solid at ambient temperature (approximately 25° C.), which exhibits a reversible solid/liquid change in state, which has a melting point of greater than approximately 40° C. which can range up to 200° C., and which exhibits, in the solid state, an anisotropic crystalline arrangement. Animal and vegetable waxes comprise, as essential constituents, esters of carboxylic acids and of alcohols with long chains. Generally, the size of the crystals of the wax is such that the crystals diffract and/or scatter light, conferring a more or less opaque cloudy appearance on the composition comprising them. By bringing the wax to its melting point, it is possible to render it miscible with oils and to form a microscopically homogeneous mixture but, on returning the temperature of the mixture to ambient temperature, recrystallization of the wax in the oils of the mixture, detectable microscopically and macroscopically (opalescence), is obtained.

Exemplary mention may be made, as waxes which can be used, of waxes of animal origin, such as beeswax, spermaceti, lanolin wax and lanolin derivatives; vegetable waxes, such as sunflower, rice or apple waxes, carnauba, candelilla, ouricury or Japan wax, cocoa butter or cork fibre or sugarcane waxes; mineral waxes, for example paraffin wax, petrolatum wax, lignite wax, microcrystalline waxes, ceresin or ozokerite; synthetic waxes, such as polyethylene waxes or Fischer-Tropsch waxes; waxy fatty acid esters; waxy fatty alcohols, such as, for example, myristyl, cetyl, stearyl, arachidyl, behenyl and erucyl alcohols and their mixtures.

The non-silicone fatty substance or substances can, for example, be present in an amount ranging from 0.1 to 90% by weight, such as from 0.5 to 60% by weight and further such as from 1 to 40% by weight, with respect to the total weight of the composition.

The surfactant or surfactants which can be used in the composition can be chosen from cationic surfactants, anionic surfactants, nonionic surfactants, amphoteric or zwitterionic surfactants and their mixtures.

The composition can, for example, comprise at least 0.01% by weight of surfactant(s), with respect to the total weight of the composition. As a further example, the composition comprises from 0.05 to 20% by weight of surfactant (s), such as from 0.1 to 10% by weight and further such as from 0.5 to 5% by weight, with respect to the total weight of the composition.

Mention may in particular be made, as example of anionic surfactants which can be used in the compositions, of (nonlimiting list) the salts (in particular alkali metal salts, especially sodium salts, ammonium salts, amine salts, aminoalcohol salts or alkaline earth metal salts (magnesium salts)) of the following compounds: alkyl sulphates, alkyl ether sulphates, alkylamido ether sulphates, alkylaryl polyether sulphates, monoglyceride sulphates; alkylsulphonates, alkyl phosphates, alkylamidesulphonates, alkylarylsulphonates, α-olefinsulphonates, paraffinsulphonates; alkyl sulphosuccinates; alkyl ether sulphosuccinates, alkylamide sulphosuccinates; alkyl sulphosuccinamates; alkyl sulphoacetates; alkyl ether phosphates, acylsarcosinates; acylisethionates and N-acyltaurates, the alkyl or acyl radical of all of these various compounds, for example, comprising from 12 to 20 carbon atoms and the aryl radical denoting, for example, a phenyl or benzyl group.

Mention may also be made, among anionic surfactants which can be used, of salts of fatty acids, such as salts of oleic acid, ricinoleic acid, palmitic acid or stearic acid; coconut oil acid or hydrogenated coconut oil acid; acyl lactylates, the acyl radical of which comprises from 8 to 20 carbon atoms.

Use may also be made of weakly anionic surfactants, such as alkyl-D-galactosideuronic acids and their salts, and also alkyl ether carboxylic acids, polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$)alkylamido ether carboxylic acids and the salts of these acids, such as those comprising from 2 to 50 ethylene oxide groups, and their mixtures.

Representative anionic surfactants, include alkyl sulphate, alkyl ether sulphate and alkyl ether carboxylate salts and their mixtures.

The cationic surfactants which can be used in the compositions comprise, for example, salts of optionally polyoxyalkylenated primary, secondary or tertiary fatty amines, quaternary ammonium salts and their mixtures.

Mention may in particular be made, as quaternary ammonium salts, of, for example:

those corresponding to the following general formula (I):

in which the radicals $R_8$ to $R_{11}$, which can be identical or different, represent a linear or branched aliphatic radical comprising from 1 to 30 carbon atoms or an aromatic radical, such as aryl or alkylaryl. The aliphatic radicals can comprise heteroatoms, such as in particular oxygen, nitrogen, sulphur and halogens. The aliphatic radicals are, for example, chosen from $C_{1-30}$ alkyl, $C_{1-30}$ alkoxy, polyoxy ($C_2$-$C_6$)alkylene, $C_{1-30}$ alkylamide, ($C_{12}$-$C_{22}$)alkylamido ($C_2$-$C_6$)alkyl, ($C_{12}$-$C_{22}$)alkyl acetate and $C_{1-30}$ hydroxyalkyl radicals; X is an anion chosen from the group of the halides, phosphates, acetates, lactates, ($C_2$-$C_6$)alkyl sulphates, or alkyl- or alkylarylsulphonates.

Representative quaternary ammonium salts of formula (I), on the one hand, can be tetraalkylammonium chlorides, such as, for example, dialkyldimethylammonium or alkyltrimethylammonium chlorides in which the alkyl radical comprises approximately from 12 to 22 carbon atoms, in particular behenyltrimethylammonium chloride, distearyldimethylammonium chloride, cetyltrimethylammonium chloride or benzyldimethylstearylammonium chloride, or also, on the other hand, to palmitylamidopropyltrimethylammonium chloride or stearamidopropyldimethyl(myristyl acetate)ammonium chloride, sold under the name Ceraphyl® 70 by Van Dyk.

imidazoline quaternary ammonium salts, such as, for example, those of the following formula (II):

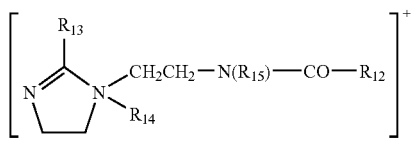 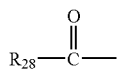 (II)

in which $R_{12}$ represents an alkenyl or alkyl radical comprising from 8 to 30 carbon atoms, for example derivatives of tallow fatty acids, $R_{13}$ represents a hydrogen atom, a $C_1$-$C_4$ alkyl radical or an alkenyl or alkyl radical comprising from 8 to 30 carbon atoms, $R_{14}$ represents a $C_1$-$C_4$ alkyl radical, $R_{15}$ represents a hydrogen atom or a $C_1$-$C_4$ alkyl radical, and $X^-$ is an anion chosen from the group of the halides, phosphates, acetates, lactates, alkyl sulphates, or alkyl- or alkylarylsulphonates. Preferably, $R_{12}$ and $R_{13}$ denote a mixture of alkenyl or alkyl radicals comprising from 12 to 21 carbon atoms, for example derivatives of tallow fatty acids, $R_{14}$ denotes a methyl radical and $R_{15}$ denotes a hydrogen atom. Such a product is sold, for example, under the name Rewoquat® W 75 by Rewo;

diquaternary ammonium salts of formula (III):

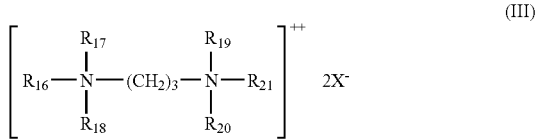 (III)

in which $R_{16}$ denotes an aliphatic radical comprising approximately from 16 to 30 carbon atoms, $R_{17}$, $R_{18}$, $R_{19}$, $R_{20}$ and $R_{21}$, which are identical or different, are chosen from a hydrogen atom and an alkyl radical comprising from 1 to 4 carbon atoms, and X is an anion chosen from the group of the halides, acetates, phosphates, nitrates and methyl sulphates. Such diquaternary ammonium salts comprise in particular propanetallowediammonium dichloride;

quaternary ammonium salts comprising at least one ester functional group, such as those of following formula (IV):

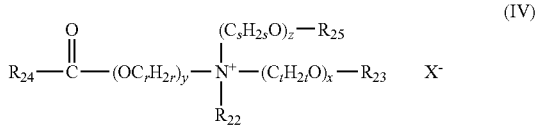 (IV)

in which:

$R_{22}$ is chosen from $C_1$-$C_6$ alkyl radicals and $C_1$-$C_6$ hydroxyalkyl or dihydroxyalkyl radicals;

$R_{23}$ is chosen from:
the

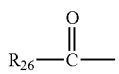

radical
saturated or unsaturated and linear or branched $C_1$-$C_{22}$ hydrocarbon radicals $R_{27}$,
the hydrogen atom, $R_{25}$ is chosen from:
the $$R_{28}-\overset{O}{\underset{\|}{C}}-$$

radical
saturated or unsaturated and linear or branched $C_1$-$C_6$ hydrocarbon radicals $R_{29}$,
the hydrogen atom, $R_{24}$, $R_{26}$ and $R_{28}$, which are identical or different, are chosen from saturated or unsaturated and linear or branched $C_7$-$C_{21}$ hydrocarbon radicals;

r, s and t, which are identical or different, are integers having values from 2 to 6;

y is an integer having a value from 1 to 10;

x and z, which are identical or different, are integers having values from 0 to 10;

$X^-$ is an organic or inorganic and simple or complex anion;

with the proviso that the sum x+y+z has a value from 1 to 15, that, when x has a value of 0, then $R_{23}$ denotes $R_{27}$ and that, when z has a value of 0, then $R_{25}$ denotes $R_{29}$.

The $R_{22}$ alkyl radicals can be linear or branched and more particularly linear.

For example, $R_{22}$ denotes a methyl, ethyl, hydroxyethyl or dihydroxypropyl radical and more particularly a methyl or ethyl radical.

For example, the sum x+y+z has a value from 1 to 10.

When $R_{23}$ is an $R_{27}$ hydrocarbon radical, it can be long and have from 12 to 22 carbon atoms or short and have from 1 to 3 carbon atoms.

When $R_{25}$ is an $R_{29}$ hydrocarbon radical, it, for example, has from 1 to 3 carbon atoms.

Representatively, $R_{24}$, $R_{26}$ and $R_{28}$, which are identical or different, are chosen from saturated or unsaturated and linear or branched $C_{11}$-$C_{21}$ hydrocarbon radicals and more particularly from saturated or unsaturated and linear or branched $C_{11}$-$C_{21}$ alkyl and alkenyl radicals.

For example, x and z, which are identical or different, have values of 0 or 1.

For example, y is equal to 1.

For example, r, s and t, which are identical or different, have values of 2 or 3 and as a further example are equal to 2.

For example, the anion can be a halide (chloride, bromide or iodide) or an alkyl sulphate, more particularly methyl sulphate. However, use may be made of methanesulphonate, phosphate, nitrate, tosylate, an anion derived from an organic acid, such as acetate or lactate, or any other anion compatible with the ammonium comprising an ester functional group.

The anion $X^-$ is more particularly still chloride or methyl sulphate.

Use, for example, can be made, in the composition according to the invention, of the ammonium salts of formula (IV) in which:

$R_{22}$ denotes a methyl or ethyl radical,
x and y are equal to 1;
z is equal to 0 or 1;
r, s and t are equal to 2;

$R_{23}$ is chosen from:
the

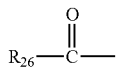

radical
methyl, ethyl or $C_{14}$-$C_{22}$ hydrocarbon radicals,
the hydrogen atom;
$R_{25}$ is chosen from:
the

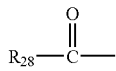

radical
the hydrogen atom;
$R_{24}$, $R_{26}$ and $R_{28}$, which are identical or different, are chosen from saturated or unsaturated and linear or branched $C_{13}$-$C_{17}$ hydrocarbon radicals and preferably from saturated or unsaturated and linear or branched $C_{13}$-$C_{17}$ alkyl and alkenyl radicals.

For example, the hydrocarbon radicals are linear.

Mention may be made, for example, of compounds of formula (IV), such as diacyloxyethyldimethylammonium, diacyloxyethyl(hydroxyethyl)methylammonium, monoacyloxyethyldi(hydroxyethyl)methylammonium, triacyloxyethylmethylammonium or monoacyloxyethyl(hydroxyethyl)dimethylammonium salts (in particular chloride or methyl sulphate), and their mixtures. The acyl radicals, for example, may have from 14 to 18 carbon atoms and originate more particularly from a vegetable oil, such as palm oil or sunflower oil. When the compound comprises several acyl radicals, the latter can be identical or different.

These products are obtained, for example, by direct esterification of triethanolamine, triisopropanolamine, alkyldiethanolamine or alkyldiisopropanolamine, optionally oxyalkylenated, with fatty acids or with mixtures of fatty acids of vegetable or animal origin, or by transesterification of their methyl esters. This esterification is followed by quaternization using an alkylating agent, such as an alkyl halide (preferably methyl or ethyl halide), a dialkyl sulphate (preferably dimethyl or diethyl sulphate), methyl methanesulphonate, methyl para-toluenesulphonate, glycol chlorohydrin or glycerol chlorohydrin.

Such compounds are sold, for example, under the names Dehyquart® by Henkel, Stepanquat® by Stepan, Noxamium® by Ceca or Rewoquat® WE 18 by Rewo-Witco.

The composition can, for example, comprise a mixture of quaternary ammonium mono-, di- and triester salts with a predominance by weight of diester salts.

Use may be made, as mixture of ammonium salts, for example, of the mixture comprising from 15 to 30% by weight of acyloxyethyldi(hydroxyethyl)methylammonium methyl sulphate, from 45 to 60% by weight of diacyloxyethyl(hydroxyethyl)methylammonium methyl sulphate and from 15 to 30% by weight of triacyloxyethylmethylammonium methyl sulphate, the acyl radicals having from 14 to 18 carbon atoms and originating from palm oil which is optionally partially hydrogenated.

Use may also be made of the ammonium salts comprising at least one ester functional group described in U.S. Pat. No. 4,874,554 and U.S. Pat. No. 4,137,180.

The nonionic surfactants which can be used in the compositions are compounds well known per se (see in particular in this respect "Handbook of Surfactants" by M. R. Porter, published by Blackie & Son (Glasgow and London), 1991, pp. 116-178). They are chosen in particular from polyethoxylated, polypropoxylated or polyglycerolated alcohols and fatty alcohols, polyethoxylated, polypropoxylated or polyglycerolated α-diols, or polyethoxylated, polypropoxylated or polyglycerolated ($C_{1-20}$)alkylphenols, the fatty chain comprising, for example, from 8 to 18 carbon atoms, it being possible for the number of ethylene oxide or propylene oxide groups to range in particular from 2 to 50 and for the number of glycerol groups to range in particular from 2 to 30.

Mention may also be made of condensates of ethylene oxide and of propylene oxide with fatty alcohols; polyethoxylated fatty amides preferably having from 2 to 30 ethylene oxide units, polyglycerolated fatty amides comprising on average from 1 to 5 glycerol groups and in particular from 1.5 to 4, ethoxylated esters of fatty acids and of sorbitan having from 2 to 30 ethylene oxide units, sucrose fatty acid esters, esters of fatty acids and of polyethylene glycol, alkylpolyglycosides, polyethoxylated vegetable oils, N—($C_{6-24}$ alkyl)glucamine derivatives or amine oxides, such as ($C_{10-14}$ alkyl)amine oxides or N—($C_{10-14}$ acyl) aminopropylmorpholine oxides.

The amphoteric or zwitterionic surfactants which can be used in the compositions of the present invention comprise, for example, aliphatic secondary or tertiary amine derivatives in which the aliphatic group is a linear or branched chain comprising from 8 to 22 carbon atoms and comprising at least one anionic group, such as, for example, a carboxylate, sulphonate, sulphate, phosphate or phosphonate group. Mention may also be made of ($C_{8-20}$)alkyl betaines, sulphobetaines, ($C_{8-20}$ alkyl) amido($C_{6-8}$ alkyl) betaines or ($C_{8-20}$ alkyl) amido($C_{6-8}$ alkyl) sulphobetaines.

Mention may be made, among amine derivatives, of the products sold under the name Miranol®, such as described in U.S. Pat. No. 2,528,378 and U.S. Pat. No. 2,781,354 and classified in the CTFA dictionary, 3rd Edition, 1982, under the names Amphocarboxyglycinate and Amphocarboxypropionate with the respective structures (1) and (2):

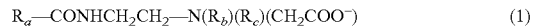

in which:
$R_a$ represents an alkyl group derived from an acid $R_a$—COOH present in hydrolysed coconut oil or a heptyl, nonyl or undecyl group,
$R_b$ represents a β-hydroxyethyl group, and
$R_c$ represents a carboxymethyl group;
and

in which:
B represents —$CH_2CH_2OX'$,
B' represents —$(CH_2)_z$—Y', with z=1 or 2,
X' represents the —$CH_2CH_2$—COOH group or a hydrogen atom,
Y' represents —COOH or the —$CH_2$—CHOH—$SO_3H$ group,
$R_a'$ represents an alkyl group of an acid $R_a'$—COOH present in hydrolysed coconut oil or in hydrolysed linseed oil, an alkyl group, such as a $C_{17}$ alkyl group and its iso form, or an unsaturated $C_{17}$ group.

These compounds are classified in the CTFA dictionary, 5th Edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

Mention may be made, by way of example, of the cocoamphodiacetate sold by Rhodia under the trade name Miranol® C2M Concentrate.

According to an exemplary embodiment, the composition according to the invention comprises the combination of one or more fatty alcohols and of one or more cationic surfactants.

In this embodiment, the fatty alcohol or alcohols comprise from 8 to 40 carbon atoms and are, for example, chosen from cetyl alcohol, stearyl alcohol and their mixtures.

The cationic surfactant or surfactants are the quaternary ammonium salts as described above, such as those comprising at least one behenyl chain.

According to another embodiment, the composition comprises the combination of petrolatum and/or of liquid petrolatum with one or more nonionic surfactants as described above.

In this embodiment, representative nonionic surfactant or surfactants are those comprising at least one oxyethylene and preferably polyoxyethylene group.

The silicones employed in the compositions can be, for example, in the soluble, dispersed or microdispersed form. The silicone or silicones are, for example, present in an amount ranging from 0.01 to 10% by weight, further such as from 0.1 to 5% by weight, with respect to the total weight of the composition.

Mention may in particular be made, as examples of silicones, of silicone oils, such as, for example, linear or cyclic polydimethylsiloxanes, and aminated silicones, such as amodimethicones.

The compositions can also comprise one or more thickening agents which can be chosen from polymeric thickeners which are natural or synthetic, anionic, amphoteric, zwitterionic, nonionic or cationic and associative or nonassociative, and nonpolymeric thickeners, such as, for example, an electrolyte or a sugar.

Mention may be made, as polymeric thickening agents, for example, of cellulose thickening agents, for example hydroxyethylcellulose, hydroxypropylcellulose and carboxymethylcellulose, guar gum and its derivatives, for example hydroxypropyl guar, sold by Rhodia under the reference Jaguar HP 105, gums of microbial origin, such as xanthan gum and scleroglucan gum, synthetic polymeric thickening agents, such as crosslinked homopolymers of acrylic acid or of acrylamidopropanesulphonic acid, for example Carbomer, or nonionic, anionic or amphoteric associative polymers, such as the polymers sold under the names Pemulen TR1 or TR2 by Goodrich, Salcare SC90 by Allied Colloids, Aculyn 22, 28, 33, 44 or 46 by Röhm & Haas and Elfacos T210 and T212 by Akzo.

The compositions can be packaged, for example, in a pot, in a tube, in a pump-action spray or in an aerosol device conventional in cosmetics.

The compositions can, when they are intended to be packaged in a device of aerosol type, comprise one or more propellant gases.

The propellant gas can then be chosen, for example, from dimethyl ether, $C_3$ to $C_5$ alkanes, halogenated hydrocarbons and their mixtures.

The compositions can additionally comprise one or more additives chosen from pearlescent agents; opacifying agents; plasticizing agents; sunscreens; fragrances; colorants; preservatives; pH-stabilizing agents; acids; bases; polyols (for example glycols); inorganic fillers; glitter, and any other additive conventionally used in the cosmetic field.

A person skilled in the art will take care to choose the optional additives and their amounts so that they do not interfere with the properties of the compositions of the present invention.

These additives can, for example, be present in the composition in an amount ranging from 0 to 50% by weight, with respect to the total weight of the composition.

The compositions can be provided, inter alia, in the form of more or less thickened liquids, of gels, of creams, of pastes or of foams.

The composition can advantageously be used for the cosmetic treatment of the hair.

It can also be used for caring for the hair, in particular in the form of a leave-in care product.

According to an embodiment, the composition is used for the styling of the hair, for example, for the simultaneous styling and conditioning of the hair.

The present disclosure also relates to a method for the cosmetic treatment of the hair, for example a hair care method, or to a method for the shaping and/or form retention of the hairstyle which consists in applying, to the hair, an effective amount of a composition as described above and in then carrying out an optional rinsing after an optional setting time.

For example, the composition is not rinsed out.

A further embodiment relates to the use, for the shaping and/or fixing of the hairstyle, of a cosmetic composition comprising, in a cosmetically acceptable aqueous medium:
one or more non-silicone fatty substances,
one or more surfactants, and
one or more vinylformamide/vinylamine copolymers comprising:
from 10 to 95 mol % of units of following formula A:

and from 90 to 5 mol % of units of following formula B:

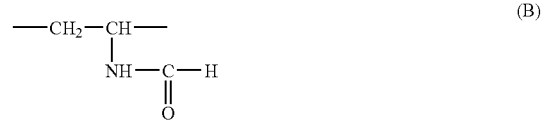

This use can be effective in reducing the volume of the hair and/or flattening the hair.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The following examples are given by way of illustration of the present invention.

EXAMPLES

In the following examples, all the amounts are given as percent by weight of active material (AM) with respect to the total weight of the composition, unless otherwise indicated.

Example 1

This example illustrates the formulation of a styling cream in accordance with the invention.

Such a cream was prepared from the ingredients shown in the table below:

| Ingredients | Contents |
|---|---|
| Vinylformamide/vinylamine copolymer (1) | 2% |
| Cetearyl alcohol | 5% |
| Myristyl/cetyl/stearyl myristate/palmitate/stearate mixture (2) | 1% |
| Behenyltrimethylammonium chloride (3) | 0.8% |
| Amodimethicone (4) | 1.5% |
| Demineralized water | q.s. 100% |

(1) Sold under the name Lupamin 9030 by BASF.
(2) Sold under the name Miracet by Laserson.
(3) Sold under the name Genamin KDMP by Clariant.
(4) Sold under the name DC 939 Emulsion by Dow Corning.

This cream has proved to be particularly appropriate for the styling and care of curly hair.

This is because the application of this cream to curly hair has made it possible to obtain the effects of reduction in volume and good definition of the curls with a lasting hold. In addition, the feel of the hair after shampooing has proved to be particularly soft and pleasant.

Example 2

This example illustrates the formulation of a styling emulsion in accordance with the invention.

Such an emulsion was prepared from the ingredients shown in the table below:

| Ingredients | Contents |
|---|---|
| Vinylformamide/vinylamine copolymer (1) | 6% |
| Liquid petrolatum (5) | 36.7% |
| White petrolatum (6) | 4% |
| Polydimethylsiloxane as an aqueous emulsion in a mixture of polyoxyethylene lauryl ethers (7) | 0.8% |
| Glycerol | 4% |
| Polyoxyethylenated sorbitan monolaurate (8) | 2% |
| Cetearyl alcohol | 2% |
| Mixture of glyceryl mono/distearate and of polyethylene glycol (100 OE) stearate (9) | 4.5% |
| Demineralized water | q.s. 100% |

(1) Sold under the name Lupamin 9030 by BASF.
(5) Sold under the name Marcol 82 by Exxon Mobil.
(6) Sold under the name Codex 236 by Aiglon.
(7) Sold under the name DC 1664 Emulsion by Dow Corning.
(8) Sold under the name Tween 20 by Uniqema.
(9) Sold under the name Arlacel 165 FL by Uniqema.

This emulsion has proved to be particularly appropriate for the styling and the care of ethnic hair.

This is because the application of this composition to straightened African hair has made it possible to obtain flattened hairstyles having a lengthy hold (hold of several days).

The application of this composition to very curly and dry hair of Brazilian hair type has made it possible to obtain very good control of the volume and beautiful definition of the curling. In addition, the feel of the hair after shampooing has proved to be particularly soft.

Comparative Example 3

The following two compositions were prepared:

| | Composition 1 (invention) | Composition 2 (outside the invention) |
|---|---|---|
| Polyvinylformamide hydrolysed at 30% (1) | 6% | — |
| N-Vinylformamide (2) | — | 6% |
| Liquid petrolatum (3) | 36.7% | 36.7% |
| White petrolatum (4) | 4% | 4% |
| Polydimethylsiloxane as an aqueous emulsion in a polyoxyethylene lauryl ethers/water mixture (5) | 0.8% | 0.8% |
| Glycerol | 4% | 4% |
| Oxyethylenated sorbitan monolaurate (6) | 2% | 2% |
| Cetearyl alcohol (7) | 2% | 2% |
| Glyceryl mono/distearate and polyethylene glycol (100 OE) stearate mixture (8) | 4.5% | 4.5% |
| Demineralized water | q.s. for 100 | q.s. for 100 |

(1) Sold under the name Lupamin 9030 by BASF.
(2) Sold under the name Lupamin 9000 by BASF.
(3) Sold under the name Marcol 82 by Exxon Mobil.
(4) Sold under the name Codex 236 by Aiglon.
(5) Sold under the name DC 1664 Emulsion by Dow Corning.
(6) Sold under the name Tween 20 by Uniqema.
(7) Sold under the name Ecorol 68/50 P by Ecogreen Oleochemicals.
(8) Sold under the name Arlacel 165 FL by Uniqema.

The two preceding compositions were applied, using 1 g of formulation per lock, to locks of wet chestnut hair weighing 2.7 g which had been shampooed, rinsed and superficially dried beforehand.

In the end, the unrinsed locks were subsequently dried under a hair dryer for 30 minutes and then disentangled.

A panel of 7 testers evaluated the cohesion of the streaking obtained with compositions 1 and 2 by categorizing them according to this criterion: rank 1 for the lock with the hair exhibiting the most cohesive streaking and rank 2 for the lock with the hair exhibiting the least cohesive streaking.

The 7 evaluators found a more cohesive streaking with composition 1 according to the invention.

The sum of the ranks obtained for each composition is: 7 for composition 1 and 14 for composition 2.

According to the Kramer test (A non parametric ranking method for the statistical evaluation of sensory data, Chemical Senses and Flavor (1974), 121-123), two compositions are significantly different at the 5% threshold if the sum of the ranks lies outside the range from 8 to 13.

As 7 is below the 8-13 range, the cohesion of the streaking is significantly greater with composition 1 according to the invention.

What is claimed is:

1. A cosmetic composition comprising, in a cosmetically acceptable aqueous medium:
   one or more non-silicone fatty substances present in an amount ranging from 0.1% to 40% by weight, relative to the total weight of the composition, wherein the fatty substances are chosen from fatty alcohols having from 8 to 40 carbons atoms,
   one or more cationic surfactants present in an amount ranging from 0.5% to 5% by weight, relative to the total weight of the composition, wherein the cationic surfactants are chosen from those corresponding to formula (I) below:

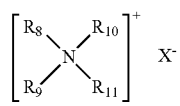
(I)

wherein
   $R_8$ to $R_{11}$, which may be identical or different, are chosen from linear or branched $C_1$-$C_{30}$ alkyl groups, and
   X is an anion chosen from halides,
   one or more vinylformamide/vinylamine copolymers present in an amount ranging from 0.5% to 10% by weight, relative to the total weight of the composition comprising:
   from 20 mol % to 40 mol % of units for following formula A:

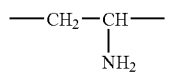
(A)

and from 60 mol % to 80 mol % of units of following formula B:

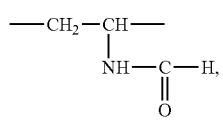
(B)

and
   one or more silicones chosen from linear or cyclic polydimethylsiloxanes and aminated silicones, present in an amount ranging from 0.1% to 5% by weight, relative to the total weight of the cosmetic composition.

2. The composition according to claim 1, characterized in that the one or more vinylformamide/vinylamine copolymers comprise one or more additional monomer units, the latter representing less than 20 mol % of the copolymer.

3. The composition according to claim 1, characterized in that the one or more vinylformamide/vinylamine copolymers consist solely of units of formula A and of units of formula B.

4. The composition according to claim 1, further comprising one or more surfactants chosen from anionic surfactants chosen from:
   the salts of the following compounds;
   alkyl sulphates,
   alkyl ether sulphates,
   alkylamido ether sulphates,
   alkylaryl polyether sulphates,
   monoglyceride sulphates;
   alkylsulphonates,
   alkyl phosphates,
   alkylamidesulphonates,
   alkylarylsulphonates,
   α-olefinsulphonates,
   paraffinsulphonates,
   alkyl sulphosuccinates;
   alkyl ether sulphosuccinates,
   alkylamide sulphosuccinates;
   alkyl sulphosuccinamates,
   alkyl sulphoacetates,
   alkyl ether phosphates,
   acylsarcosinates;
   acylisethionates and N-acyltaurates;
   salts of fatty acids and acyl lactylates, the acyl radical of which comprises from 8 to 20 carbon atoms;
   alkyl-D-galactosideuronic acids and their salts,
   alkyl ether carboxylic acids,
   polyoxyalkylenated ($C_6$-$C_{24}$)alkyl ether carboxylic acids,
   polyoxyalkylenated ($C_6$-$C_{24}$)alkylaryl ether carboxylic acids, and polyoxyalkylenated ($C_6$-$C_{24}$)alkylamido ether carboxylic acids and
   the salts of the acids chosen from alkyl ether carboxylic acids,
   polyoxyalkylenated ($C_6$-$C_{24}$)alkyl ether carboxylic acids and their salts,
   polyoxyalkylenated ($C_6$-$C_{24}$)alkylaryl ether carboxylic acids and their salts, and
   polyoxyalkylenated ($C_6$-$C_{24}$)alkylamido ether carboxylic acids and their salts.

5. The composition according to claim 4, characterized in the at least one or more anionic surfactants are chosen from alkyl sulphate, alkyl ether sulphate, and alkyl ether carboxylate salts.

6. The composition according to claim 1, further comprising one or more surfactants chosen from nonionic surfactants chosen from:
   polyethoxylated, polypropoxylated and polyglycerolated alcohols and fatty alcohols,
   polyethoxylated, polypropoxylated and polyglycerolated α-diols, and
   polyethoxylated, polypropoxylated and polyglycerolated ($C_{1-20}$)alkylphenols,
   characterized in that the fatty chain comprises from 8 to 18 carbon atoms, it being possible for the number of ethylene oxide or propylene oxide groups to range from 2 to 50 and for the number of glycerol groups to range from 2 to 30;
   condensates of ethylene oxide and of propylene oxide with fatty alcohols;
   polyethoxylated fatty amides having from 2 to 30 ethylene oxide units,
   polyglycerolated fatty amides comprising on average from 1 to 5 glycerol groups, ethoxylated esters of fatty acids and of sorbitan having from 2 to 30 ethylene oxide units,
sucrose fatty acid esters,
esters of fatty acids and of polyethylene glycol,
alkylpolyglycosides,
polyethoxylated vegetable oils,
N—($C_{6-24}$ alkyl)glucamine compounds and
Amine oxides.

7. The composition according to claim 6, characterized in that the amine oxides are chosen from ($C_{10-14}$alkyl)amine oxides and N—($C_{10-14}$ acyl)aminopropylmorpholine oxides.

8. The composition according to claim 1, further comprising at least one or more surfactants chosen from:
aliphatic secondary and tertiary amines in which the aliphatic group is chosen from linear and branched chains comprising from 8 to 22 carbon atoms and comprising at least one anionic group;
($C_{8-20}$)alkyl betaines, sulphobetaines, ($C_{8-20}$ alkyl) amido ($C_{6-8}$ alkyl) betaines and ($C_{8-20}$ alkyl) amido($C_{6-8}$ alkyl) sulphobetaines.

9. The composition according to claim 8, characterized in that said at least one anionic group is chosen from carboxylate, sulphonate, sulphate, phosphate, and phosphonate groups.

10. The composition according to claim 1, characterized in that the one or more non-silicone fatty substances are chosen from fluid fatty alcohols comprising from 8 to 26 carbon atoms.

11. The composition according to claim 1, characterized in that said composition further comprises at least 10% by weight of water, with respect to the total weight of the composition.

12. The composition according to claim 1, characterized in that the cosmetically acceptable medium further comprises one or more cosmetically acceptable organic solvents chosen from lower $C_1$-$C_4$ alcohols; polyols; polyol ethers; $C_5$-$C_{10}$ alkanes, $C_3$-$C_4$ ketones; $C_1$-$C_4$ alkyl acetates; dimethyloxyethane and diethoxyethane.

13. The composition according to claim 1, characterized in that said composition further comprises one or more thickening agents.

14. The composition according to claim 1, characterized in that said composition additionally comprises one or more propellant gases.

15. The composition according to claim 1, characterized in that said composition further comprises one or more additives chosen from pearlescent agents; opacifying agents; plasticizing agents; sunscreens; fragrances; colorants; preservatives; pH-stabilizing agents; acids; bases; polyols; inorganic fillers; glitter, and any other additive conventionally used in the cosmetic field.

16. The composition according to claim 1, characterized in that said composition is provided in the form of a thickened liquid, of a gel, of a cream, of a paste or of a foam.

17. A method for the cosmetic treatment of the hair, characterized in that it comprises applying, to the hair, an effective amount of a composition comprising, in a cosmetically acceptable aqueous medium:
one or more non-silicone fatty substances present in an amount ranging from 0.1% to 40% by weight, relative to the total weight of the composition, wherein the fatty substances are chosen from fatty alcohols having from 8 to 40 carbons atoms,
one or more cationic surfactants present in an amount ranging from 0.5% to 5% by weight, relative to the total weight of the composition, wherein the cationic surfactants are chosen from those corresponding to formula (I) below:

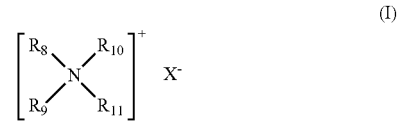

wherein
$R_8$ to $R_{11}$, which may be identical or different, are chosen from linear or branched $C_1$-$C_{30}$ alkyl groups, and
X is an anion chosen from halides,
one or more vinylformamide/vinylamine copolymers present in an amount ranging from 0.5% to 10% by weight, relative to the total weight of the composition comprising:
from 20 mol % to 40 mol % of units of following formula A:

and from 60 mol % to 80 mol % of units of following formula B:

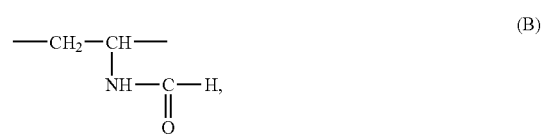

and
one or more silicones chosen from linear or cyclic polydimethylsiloxanes and aminated silicones, present in an amount ranging from 0.1% to 5% by weight, relative to the total weight of the composition,
and then carrying out an optional rinsing after an optional setting time.

18. The method according to claim 17, wherein said composition is not rinsed out.

19. A method for shaping and/or fixing of the hairstyle, comprising applying to hair a cosmetic composition comprising, in a cosmetically acceptable aqueous medium:
one or more non-silicone fatty substances present in an amount ranging from 0.1% to 40% by weight, relative to the total weight of the composition, wherein the fatty substances are chosen from fatty alcohols having from 8 to 40 carbons atoms,
one or more cationic surfactants present in an amount ranging from 0.5% to 5% by weight, relative to the total weight of the composition, wherein the cationic surfactants are chosen from those corresponding to formula (I) below:

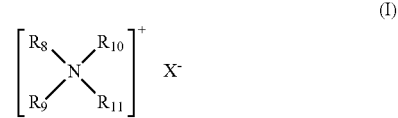

wherein
$R_8$ to $R_{11}$, which may be identical or different, are chosen from linear or branched $C_1$-$C_{30}$ alkyl groups, and
X is an anion chosen from halides, and
one or more vinylformamide/vinylamine copolymers present in an amount ranging from 0.5% to 10% by weight, relative to the total weight of the composition comprising:
from 10 mol % to 95 mol % of units of following formula A:

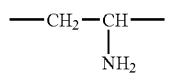
(A)

and from 90 mol % to 5 mol % of units of following formula B:

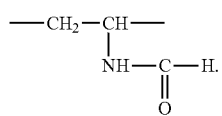
(B)

20. The method according to claim 19, wherein the cosmetic composition is applied to the hair to reduce the volume of the hair and/or to flatten the hair.

21. A method for caring for the hair comprising applying to the hair a cosmetic composition comprising, in a cosmetically acceptable aqueous medium:
one or more non-silicone fatty substances present in an amount ranging from 0.1% to 40% by weight, relative to the total weight of the composition, wherein the fatty substances are chosen from fatty alcohols having from 8 to 40 carbons atoms,
one or more cationic surfactants present in an amount ranging from 0.5% to 5% by weight, relative to the total weight of the composition, wherein the cationic surfactants are chosen from those corresponding to formula (I) below:

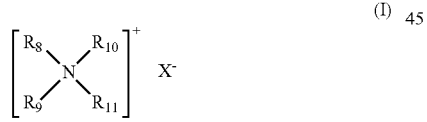
(I)

wherein
$R_8$ to $R_{11}$, which may be identical or different, are chosen from linear or branched $C_1$-$C_{30}$ alkyl groups, and
X is an anion chosen from halides,
one or more vinylformamide/vinylamine copolymers present in an amount ranging from 0.5% to 10% by weight, relative to the total weight of the composition comprising:
from 20 mol % to 40 mol % of units of following formula A:

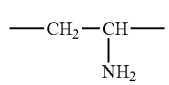
(A)

and from 60 mol % to 80 mol % of units of following formula B:

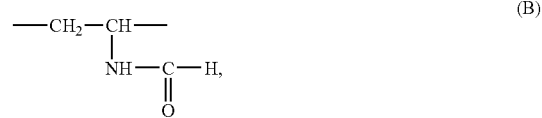
(B)

and
one or more silicones chosen from linear or cyclic polydimethylsiloxanes and aminated silicones, present in an amount ranging from 0.1% to 5% by weight, relative to the total weight of the cosmetic composition.

22. The method according to claim 21, wherein said composition is in the form of a leave-in care product.

23. A method for simultaneously styling and conditioning the hair comprising applying to the hair a cosmetic composition comprising, in a cosmetically acceptable aqueous medium:
one or more non-silicone fatty substances present in an amount ranging from 0.1% to 40% by weight, relative to the total weight of the composition, wherein the fatty substances are chosen from fatty alcohols having from 8 to 40 carbons atoms,
one or more cationic surfactants present in an amount ranging from 0.5% to 5% by weight, relative to the total weight of the composition, wherein the cationic surfactants are chosen from those corresponding to formula (I) below:

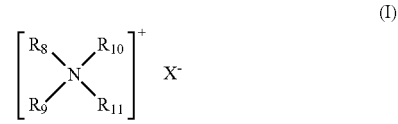
(I)

wherein
$R_8$ to $R_{11}$, which may be identical or different, are chosen from linear or branched $C_1$-$C_{30}$ alkyl groups, and
X is an anion chosen from halides,
one or more vinylformamide/vinylamine copolymers present in an amount ranging from 0.5% to 10% by weight, relative to the total weight of the composition comprising:
from 20 mol % to 40 mol % of units of following formula A:

(A)

and from 60 mol % to 80 mol % of units of following formula B:

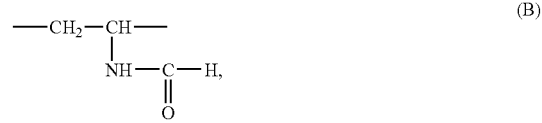
(B)

and optionally one or more silicones chosen from linear or cyclic polydimethylsiloxanes and aminated silicones, present in an amount ranging from 0.1% to 5% by weight, relative to the total weight of the cosmetic composition.

* * * * *